United States Patent [19]
Born et al.

[11] Patent Number: 6,033,644
[45] Date of Patent: *Mar. 7, 2000

[54] BIOMODULATORS AS UNIVERSAL IMAGING AGENTS

[75] Inventors: Jerry L. Born; Dennis Eshima; Paul L. Mann; Nicholas A. Matwiyoff, all of Albuquerque, N.Mex.

[73] Assignee: University of New Mexico, Albuquerque, N.Mex.

[*] Notice: This patent is subject to a terminal disclaimer.

[21] Appl. No.: 09/186,096

[22] Filed: Nov. 5, 1998

Related U.S. Application Data

[62] Division of application No. 08/405,017, Mar. 16, 1995, Pat. No. 5,906,807, which is a division of application No. 07/694,325, May 1, 1991, Pat. No. 5,401,489.

[51] Int. Cl.⁷ .............................. A61K 51/04; A61B 5/055
[52] U.S. Cl. ...................... 424/1.57; 424/1.11; 424/1.41; 424/1.65; 424/1.73; 424/9.3; 424/9.36; 424/9.4; 424/9.43; 424/9.35
[58] Field of Search .................................... 424/9.4, 9.42, 424/9.43, 1.41, 1.57, 1.65, 1.73, 9.3, 9.36, 9.35, 1.45, 1.49, 9.1, 9.5, 9.6, 1.11

[56] References Cited

U.S. PATENT DOCUMENTS

| | | | |
|---|---|---|---|
| 5,021,427 | 6/1991 | Elbein et al. | 514/315 |
| 5,047,227 | 9/1991 | Rodwell et al. | 424/1.1 |
| 5,140,693 | 8/1992 | Born et al. | 424/4 |
| 5,277,892 | 1/1994 | Rhodes | 424/169 |

OTHER PUBLICATIONS

"Evaluation of biological response modifiers in the enhancement of . . . ", M.L. Thakur et al., *J. Immun. Methods.*, vol. 152, 1992, pp. 209–216.

"Cell Surface Oligosaccharide Modulation During Differentiation" IV. . . . , Paul L. Mann et al., *Mech. of Ageing & Develop.*, vol. 44, 1988, pp. 17–33.

"Membrane Oligosaccharides: Structure and Function during . . . ", Paul L. Mann, *Intl. Rev. Cytol.*, vol. 112, 1988, pp. 67–95.

*Primary Examiner*—Jose' G. Dees
*Assistant Examiner*—Michael G. Hartley
*Attorney, Agent, or Firm*—Judith A. Evans; Dovetail Technologies Inc.

[57] ABSTRACT

Biomodulators, optionally linked to imaging-active moieties, can be administered to a host to enhance images thereof, e.g., NMR-, X-ray- or radio-images, preferably by increasing aberrant tissue signal intensity. Biomodulators can also condition tissue to enhance uptake of otherwise non-specific imaging agents. When linked to drugs, biomodulators can target the same to particular sites in the body.

14 Claims, 9 Drawing Sheets

BIOMODULATORS AS UNIVERSAL IMAGING AGENTS

This application is a division of Ser. No. 08/405,017, filed Mar. 16, 1995, U.S. Pat. No. 5,906,807, which is a division of Ser. No. 07/694,325 filed May 1, 1991 which issued as U.S. Pat. No. 5,401,489, which are all incorporated herein by reference in their entirety.

This application is related to [Attorney's Docket Numbers UNMEX 2, UNMEX 4 and UNMEX 5], all entirely incorporated by reference herein.

BACKGROUND OF THE INVENTION

One of the most difficult problems in in vivo imaging of living organisms is how to distinguish between normal and aberrant tissue. Many approaches to this problem have been developed, including inter alia, X-ray imaging (including CAT-scanning), radionuclide imaging, fluoroscopy, ultrasonic imaging and nuclear magnetic resonance (NMR) imaging (MRI), with and without the administration of imaging agents, e.g., contrast media. The imaging agent may comprise materials which are themselves opaque to the detection signal and simply increase the contrast between organs or tissues containing it and organs or tissues which do not, e.g., as with X-ray agents. Alternatively, the agent can be one which has a local effect on the endogenous moiety active to the modality, as in the effect of NMR contrast agents on protons in vivo. For example, such agents may comprise materials which are selectively biodistributed due to pharmacokinetics or affinity for a certain compound, cell type, tissue, organ, etc. In the latter case, the agent will highlight those areas containing the matter for which the agent has affinity; in the former, it will highlight the areas where it is selectively transported. Many such imaging agents are well known in the relevant arts, as are methods of use thereof.

Each of the known agents and methods suffers from a variety of deficiencies related to tolerability of the imaging agent, invasive nature of the active radiation and efficiency and accuracy of the diagnosis enabled by the resulting image. For example, NMR imaging is the most safe in terms of the radiation used. It does not involve ionizing radiation as does X-ray. Under many circumstances it provides very detailed information by imaging of various tissues. However, it suffers from a limitation based upon the lack of distinction between normal and aberrant tissue which has the same NMR signature. Although several approaches have been taken toward increasing the specificity of NMR contrast agents (usually involving paramagnetic compounds, often in combination with targeting agents, e.g., antibodies), these are limited in that they rely on administration of materials, e.g., antibodies, whose in vivo specificity must be determined in advance of application. The known NMR contrast agents, such as, e.g., gadolinium-DTPA, are not universally specific for all abnormal vs. normal tissue. What is needed is a contrast agent which is specific for aberrant tissue vs. its normal tissue counterpart, to as universal an extent as possible, and which can correspondingly be used substantially non-specifically, i.e., as universally as possible, to locate and diagnose aberrant tissues in a large proportion of the body of a living organism.

SUMMARY OF THE INVENTION

The present invention provides methods of imaging comprising administering an imaging-effective amount of a biomodulator, e.g., of enhancing the contrast of an NMR image of abnormal tissue of a host, comprising administration to a host of an amount of a biomodulator effective to enhance said contrast, e.g., wherein abnormal tissue of the host has enhanced contrast.

In a more general aspect, this invention provides a method of imaging tissue, preferably abnormal tissue, comprising administering a biomodulator, optionally labelled with a moiety detectable by a selected imaging modality, or optionally administered in conjunction with an imaging-active agent whose biodistribution is changed by the administration of a biomodulator, in an amount effective to image the tissue.

For MRI, as indicated above, no label is necessary. The biomodulators of this invention selectively biodistribute in certain tissue whereby they modify the distribution of water (protons detectable by MRI) in the local environment, thereby producing an image of the environment which is different from that of the environment without biomodulator mediation. This difference alone will provide diagnostically useful information in MRI.

In another aspect, this invention provides a method of delivering a drug to a particular site in a body of a host containing abnormal tissue comprising administering a biomodulator and said drug, the amounts of said biomodulator and said drug being effective to selectively concentrate said drug at said site of abnormal tissue.

BIOMODULATORS

Figure 1:
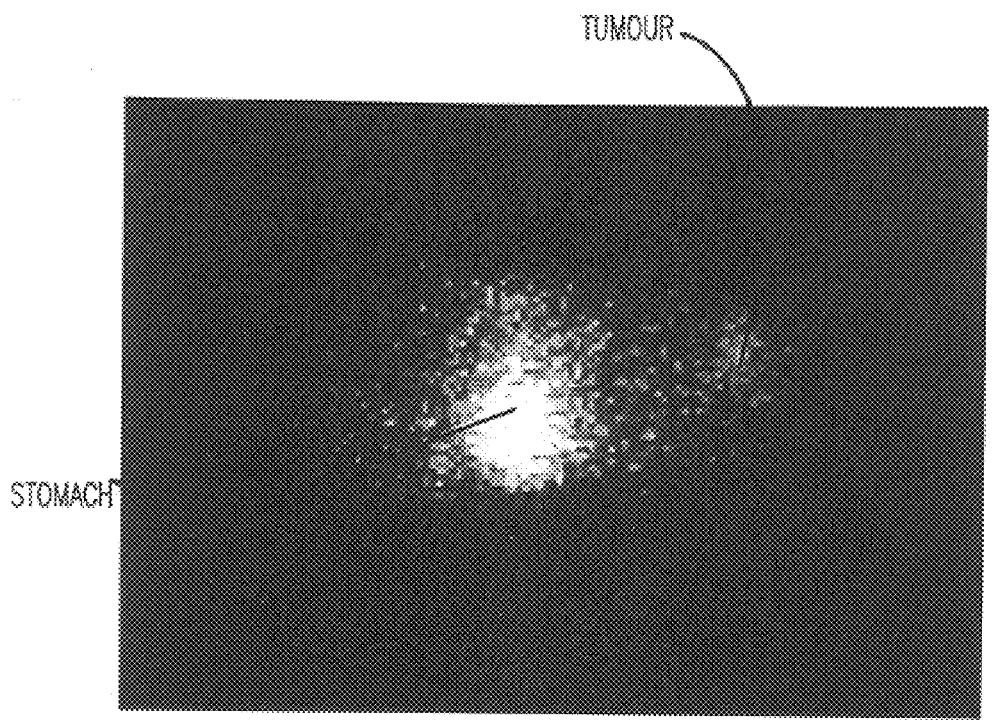
FIGS. 1 and 2 are radionuclide images of mice that were injected with allogenic B-16 melanoma cells on days 7 and 10, respectively, prior to the injection of $^{99m}$TC-labeled pokeweed mitogen (Tc-PWM). Images were taken four hours post injection of Tc-PWM.

Biomodulators are natural products or synthetic compounds, e.g., analogs of a natural product which perturb the normal cellular differentiative and proliferative activity of eucaryotic, particularly mammalian, particularly human, cells. This biomodulatory activity is non-cell-lineage specific, affecting differentiation and proliferation in substantially all species and substantially all cell types. The activity of these compounds is considered to be at a primitive level of cellular control, common to all cells, and the compounds are therefore non-specific in their effect and production by cells. Thus, biomodulators as defined herein are distinct from so-called "biological response modifiers," such as, e.g., interleukins, interferons and other "kines," which have highly specific activities, and which are specific natural products of specific stimuli produced by specific highly specialized cell types.

Without wishing to be bound by theory, it is believed that the activity of biomodulators is based upon a generic, cell-surface oligosaccharide dependent model for "primitive" phenotypic expressions of differentiation. This theory is discussed in P. L. Mann, Intl. Rev. Cytol. 12, 67–95 (1988), which is incorporated herein by reference.

Preferred "biomodulators" include compounds selected from
(a) a compound of formula (I)

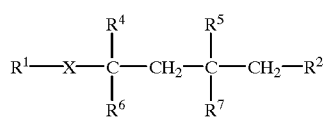

wherein
$R^1$ is an optionally substituted aromatic, cycloaliphatic or heterocyclic ring system,
$R^2$ is —$CH_2OH$, —CHO, —$COOR^3$, —$COSR^3$, —$CONR^8R^9$ or the corresponding lactone

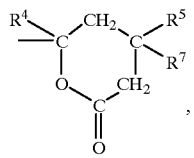

wherein
$R^3$ is H or $C_{1-10}$-alkyl,
$R^4$ and $R^5$ are each independently H or $C_{1-6}$-alkyl,
$R^6$ and $R^7$ are each independently OR, NHR or SR wherein R is H or $C_{1-4}$-alkanoyl,
$R^8$ and $R^9$ are each independently H or $C_{1-10}$-alkyl, and
X is $C_{2-3}$-alkylene, $C_{2-3}$-alkenylene, $C_{2-3}$-alkynylene, a cyclopropylene group, —$OCH_2$— or —$SCH_2$—;
(b) a compound of formula (II) (swainsonine)

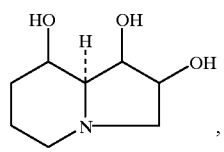

or an indolizidine alkaloid having an electonically similar 1,3-diol structure;
(c) cellular activator and differentiator (CAD); and
(d) pokeweed mitogen; and having the biological activity of a biomodulator as described herein.

A first category of compounds useful in the methods of the present invention comprises compounds of formula (I) as described above. Particularly preferred compounds within the scope of formula (I) are those which have a steric configuration at the 3,5-carbon atoms of the heptanoic or octanoic acid based diol chain which is substantially electronically similar to that of the 3S,5R, 3S,5S or 3R,5R configurations of colletruncoic acid. By "substantially electronically similar" is meant that in the energy minimized form, the interhydroxyl distance between the relevant hydroxyl groups is between 4.2–4.4 Å, preferably about 4.3 Å. The electronic similarity of the compounds can be determined, e.g., by performing routine energy minimization calculations, e.g., utilizing conventional calculations, such as those performed by the Chemdraft Computational Package, program MM-2, (C-Graph Software, Inc., Austin, Tex. 78763). In general, compounds which have a configuration 3R,5S (when X is an alkylene group, i.e., is saturated) or equivalently 3S,5R (when X is an alkenylene or alkynylene group, i.e., is unsaturated) will correspond to this most preferred structure. 3R,5R- and 3S,5S-configurations are also preferred.

The radical $R^1$ has a variable effect. In general, the $R^1$ radical is substantially hydrophobic with well defined pockets of electronegativity. Suitable $R^1$ ring groups have 1–4 or more fused and/or covalently bonded rings, optionally substituted by substituents which render this portion of the molecule electronegative (e.g., OH, halo, $NO_2$, $NH_2$, COOH, etc.). The compounds of formula I can possess $R^1$ ring groups having a hydrophobicity and/or electronegativity on the order of those of one or more of the following suitable $R^1$ rings, including $C_{6-25}$ mono-, bi-, tri- or polynuclear-aryl, -aryloxy, -cycloalkyl, -cycloalkenyl, -cycloalkadienyl, etc., as well as heterocyclic rings containing or sharing one or more, e.g., 2 or 3, O, S or N atoms. Where fused systems containing 1–4 or more individual rings are involved, each ring generally contains 4–7 atoms, 1–3, preferably, 1–2, of which are O, N or S atoms, the remainder being C atoms, these generally having 1–4 hetero atoms in total. Thus, heteroaryl and hydroheteroaryl groups are suitable. Examples of suitable $R^1$ groups include benzyl, benzyloxy, phenyl, phenyloxy, naphthyl, naphthyloxy, tetrahydronaphthyl, hexahydronaphthyl, octahydronaphthyl, imidazolyl, pyrimidyl, pyrazolyl, indenyl, quinolinyl, pyrrolyl, indolyl, indolizinyl, etc.

In addition, particularly preferred compounds of formula (I) are those in which n is 1, $R^2$ is $COOR^3$ or the corresponding lactone, $R^4$ and $R^5$ are each H, $R^6$ and $R^7$ are each OH, and X contains a cis or trans double bond.

One subtype of these compounds useful in the methods of the present invention are relatively small (for example, molecular weight less than 1,000 daltons) naturally occurring compounds (in isolated form) having the structure of formula I and the required electronic structure at the 3,5-carbon atoms. For example, the appropriate enantiomer of colletruncoic acid as defined above,

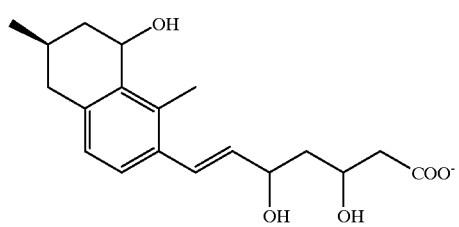

a natural compound isolated from *Colletotrichum truncatum*, has a structure encompassed by the structural formula described above and has been shown to have biomodulator activity. Colletruncoic acid can be isolated according to the method outlined in Stoessl et al. Z. Naturforsh. 41c, 677–680 (1986), except as modified in that Stoessl et al. described the natural product as being a racemic methylester, which is incorrect; the correct compound is a free acid of one enantiomer with the noted stereochemistry.

Another subtype of these compounds are synthetic compounds of formula I having the required electronic structure at the 3,5-carbon atoms, as described above. All compounds of formula I can be made, in general, from readily available and/or preparable starting materials according to routine chemical syntheses, for example, according to methods outlined in U.S. Pat. Nos. 4,755,606, 4,613,610, 4,255,444, 4,248,889, 4,761,419, 4,751,235, 4,198,425, 4,137,322, 3,983,140, 4,588,715, 4,710,513, 4,739,073, 4,681,893; WO 84/92903; WO 87/02662; WO 88/01997; and WO 86/03488. For joining $R^1$—X—C (wherein C is the rest of the molecule) when X is $CH_2CH_2$, see Tetrahedron, 42, 4909–4951 (1986). For joining $R^1$—X—C when X is —CH═CH—, a selenoxide or sulfoxide coupling and elimination strategy can be employed (see J. Org. Chem., 51, 648–657 (1986)) or, alternatively, Wittig methodology (see J. Org. Chem., 49, 3994–4003 (1984). When X is —C≡C—, the acetylide $R^1$—C≡C⁻ can be added to an appropriate aldehyde or ketone. When X is —$OCH_2$— or —$SCH_2$— then $R^1O^-$ or $R^1S^-$ will be condensed with an appropriate electrophile; see Tetrahedron Lett., 29, 2563–2566 (1988). Similarly, the $R^1$ moieties bearing substituted groups can be synthesized either before or after linkage to the remainder of the molecule.

A second general category of compounds having a related structure and having biomodulator activity is constituted by other small, naturally occurring compounds such as, e.g., swainsonine,

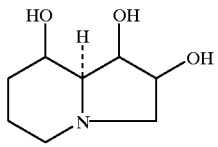

which is a low molecular weight indolizidine alkaloid extracted from Swainsona sp. as well as from a number of other natural sources, and has hydroxy groups on its ring which have an almost identical electronic structure to the hydroxy groups on the heptanoate chain as described above. (Swainsonine is known to have anticancer effects possibly mediated through its inhibition of α-mannosidase II; thus, this effect is not suggestive of its biomodulator role or its range of activities in the other utilities described above. See, e.g., Newton, S. A., et al., J. Natl. Cancer Inst. 81, 1024–1033 (1989); Dennis, J. W., et al., Cancer Res. 50, 1867–1872 (1990).) Swainsonine is commercially available, e.g., from Boerringer-Mannheim, or can be isolated according to the method outlined in Hino, M., et al., J. Antibiotics 38, 926–935 (1985). Other members of this category are, e.g., other indolizidine alkaloid compounds retaining the electronic structure of the important "1,3-diol array" of swainsonine, such as swainsonine substituted in the ortho and meta positions on the 6-membered ring by hydroxy groups (castanospermine) and other natural products having an electronically similar 1,3 diol array. Still other suitable alkaloids are related compounds having two 6-membered rings or two 5-membered rings.

In addition to the known natural low molecular weight compounds swainsonine and colletruncoic acid, a third major type of biomodulator is a new compound provided by the present invention having properties similar to the compounds of Formula I. This compound, cellular activator and differentiator or CAD, is isolated from *Penicilium restrictum*, has a molecular weight of about 500, and is believed, without wishing to be bound by theory, to have a similar structure to colletruncoic acid. It can be isolated according to the method outlined in [Attorney's Docket UNMEX 2.].

A fourth category of compounds useful in the methods of the present invention are high molecular weight compounds having biomodulator activity, such as pokeweed mitogen (PWM), which is a well known mixture of five isomitogenic glycopeptides extracted from *Phytolacca americana*, and which is known for its ability to stimulate cellular proliferation. Although its structural relationship to the above described compounds is uncertain, PWM is thought to interact with cells in a similar way and has the same spectrum of effects for the various utilities disclosed herein. Pokeweed mitogen can be isolated according to well-known methods, e.g., according to the method outlined in Riesfeld, R. A., et al., Proc. Natl. Acad. Sci. (U.S) 58, 2020–2027 (1967). It is noted that the differentiative and proliferative activities of PWM can be separated, i.e., by separating the isotypes, e.g., according to the method of Waxdal, M. J., Biochem. 13, 3671 (1974). The differentiative substance is preferred.

Preferred compounds include 3S,5R-colletruncoic acid and the compound obtained by switching the heptanoate chain of 3S,5R-colletruncoic acid with the adjacent methyl group on the ring.

Biomodulator Activities

Cellular functions can be broadly divisible into two general categories: proliferation (reproduction) and differentiation (specialization of function). According to present theory, the proliferative function is continuously present in the normal cell, and is dominated in the mature cell by the differentiative function, which thus acts as an integrative force to regulate both differentiative and proliferative functions in the mature cell. A failure in the biochemical mechanisms upon which the cell is dependent for control of cell differentiative and proliferative functions thus has important implications, as disruption of normal differentiative and proliferative controls may result in both abnormal cellular function and abnormal cellular growth regulation. Thus, improperly enhanced cellular proliferation, particularly when coupled to impaired cellular differentiation may be a basis for neoplasia. Similarly, the well-known phenomenon of cellular senescence couples a failure of proliferation of terminally differentiated cells after a defined number of cellular generations.

Without wishing to be bound by theory, biomodulators exert their effects at the most fundamental level by influencing cellular differentiation behavior, particularly abnormalities therein. They, for instance, can induce differentiation by modulating expression of the cellular differentiative phenotype; inter alia, the biomodulators induce expression of unexpressed genes to significantly diversity cellular function, or to significantly increase existing cellular function. The biomodulators are believed to induce proliferation in senescent cells by biomodulating expression of the cellular proliferative phenotype by similar mechanisms. Overall, the biomodulators counteract aberrant proliferative or differentiative cellular function by stimulating intracellular biochemical controls to normalize cellular behavior. It is this ability of biomodulators to normalize abnormal cellular function, both differentiative and proliferative (usually indirectly by normalizing aberrant differentiative activity underlying the aberrant proliferation, but also directly, e.g., in the case of senescent cells), across a wide spectrum of cell types, which primarily underlies their usefulness.

The biomodulators effect their results in very low concentrations and are generally characterized by a relatively low (less than 1,000 daltons) molecular weight, higher weights, however, also being involved in some cases. The compounds are non-toxic in the amounts employed in the methods of the present invention. It is theorized that these compounds simulate or involve mechanisms controlling cellular differentiative behavior and/or integration of cell proliferation and differentiation activity on a primitive level, thus accounting for their influence on a broad range of biological effects.

As mentioned, one of the effects which biomodulators have been demonstrated to possess is their ability to normalize cellular function in cells which have become aberrant, e.g., tumor cells or senescent cells. In particular, from a mechanistic perspective, it has been shown that administration of biomodulators affects the conformational arrangements of simple cell-surface oligosaccharide structures in aberrant cells (Mann, P. L., et al., Mech. Ageing Devel. 44, 17–33 (1988)). This has been shown, for example, by determination of binding-class affinities and capacities for specific lectin/oligosaccharide combinations, with and without biomodulator influence. Scatchard analysis and the calculation of Gibb's Free Energy ($\Delta G$) were used for comparison purposes, as disclosed therein. The $\Delta G$ values obtained were found to be predictors of phenotypic changes and the efficacy of the biomodulators.

Characterization of the nature of these effects on the conformation of the cell-surface oligosaccharide displays was performed, inter alia, by NMR spectroscopy on cells in culture, both aberrant and normal. It was found that cells which are about to undergo senescence, and thus are failing in their proliferative function, showed a significant narrowing in proton line width measurements of cell surface water, which was correlated with a "down-regulation" of the $\Delta G$ value of the cell surface oligosaccharide display. Treatment of the cells with biomodulators prevented the "down-regulation" and NMR proton line width changes, as well as the subsequent development of the senescent phenotype. On the other hand, neoplastic cells have cell surface oligosaccharide displays which are "in-between" those of normal and senescent cells, both in terms of $\Delta G$ values and the proton line widths. Treatment of these cells with biomodulators "up-regulates" the oligosaccharide conformations, increases line width values, increases the ability of these cells to be recognized by cytotoxic lymphocytes (the normal phenotype) and decreases their generation times in vitro.

Typically, the biomodulators will selectively accumulate in areas of the body containing abnormal tissue. This occurs because of the ability of biomodulators to normalize aberrantly differentiating cells. Thus, the biomodulators will concentrate in and around such cells on which they are active, whereby they are particularly useful for imaging diseased or otherwise abnormal tissue, thus providing a method for facilitating the staging thereof. In the cases where a biomodulator concentrates in normal tissue, which particular tissue is the target of a particular biomodulator will be routinely determinable by preliminary experiments involving administration of the biomodulator followed by conventional body scans.

In MRI, imaging enhancement occurs inherently due to concomitant changes in the water distribution around the tissue in which the biomodulator concentrates due to the presence of the biomodulator. Typically, the amount of water in the biomodulator-containing tissue will be increased. This is particularly true in the case of tumors whose images are dramatically intensified by this invention. Where the amount of water is decreased, relative to the background, contrast will, of course, still be enhanced for the image of the abnormal or other biomodulator-containing tissue due to the resultant differential intensity produced in MRI. For MRI, the underlying physical phenomenon being measured can be any of the known parameters including $T_1$, $T_2$, proton density, chemical shift, etc.

Because of the ability of biomodulators to selectively concentrate in abnormal or other tissue, they can be used as "targeting molecules," analogously to the use of other targeting moieties such as monoclonal antibodies or fragments thereof, lipids, etc., for conventional targeting purposes. For example, they can be coupled, conjugated or otherwise bonded to any molecule which it is desired to enhance the concentration of in such tissues. These molecules can be, for example, a specific agent, i.e., one which already possesses some inherent tissue or site specificity, such as, e.g., Gd-DTPA to tumors in MRI, TNF-$\alpha$ as described herein, radiolabeled monoclonal antibodies, etc. Other types of molecules which can be targeted include non-specific agents, e.g., one which ordinarily does not possess tissue specificity, such as human serum albumin. In addition, therapeutic agents can be targeted by linkage to biomodulators. For each of the various imaging modalities, imaging-detectible active agents include, e.g., for MRI, paramagnetic moieties, e.g., metal ions, e.g., of atomic numbers 21–29, 42, 44 and 58–70, inter alia, particularly gadolinium, dysprosium, iron, manganese, etc; for X-ray imaging, heavy metals, e.g., of atomic numbers 21–29, 42, 44 and 57–83, inter alia; for radionuclide imaging (or radiotherapy, also), radioactive ions, such as cobalt, technetium, strontium, copper, iodine, e.g., $^{123}$I or $^{131}$I, etc., and $^{111}$In. PET (positron emission tomography) via attachment of positron emitting isotopes, such as $^{43}$Sc, $^{52}$Fe, $^{55}$Co, Cu, etc. Where radioactivity is the operative modality, any of the conventional techniques for radioactivity "tagging" chemical structures can be used, e.g., as described in Crockford et al., U.S. Pat. No. 4,424,200; Rhodes, U.S. Pat. No. 4,305,922; Alvarez et al., U.S. Pat. No. 4,741,900; EP-A-0 188 256; EP-A-0 289 187; EP-A-0 203 764.

Selective localization of these "active" moieties by means of the targeting effect of the biomodulators will produce image enhancement by the corresponding modality, e.g., MRI, X-ray, radioimaging, PET imaging, etc.

"Active agent" as used herein in the context of imaging means an agent which is detectible by an imaging modality which is either bonded to a biomodulator or whose biodistribution is changed by being administered before, simultaneously with or after a biomodulator, such that the biomodulator and active agent are simultaneously bioeffective to enhance imaging by said modality. The imaging-active agent may be, inter alia, an imaging-detectible moiety per se (e.g., a radionuclide), or an imaging-detectible moiety bound by or to a carrier (e.g., a radionuclide-labeled carrier protein or paramagnetic moiety bound to a chelate). However, the chemical structure of the active agent is entirely non-critical as long as it is detectible by the imaging modality and can include simple molecules, complex molecules, polymers such as oligopeptides, polypeptides, proteins, carbohydrates, etc. In each case, the imaging-detectible moiety will be bound either to a biomodulator, or to another moiety, such that the biodistribution of the imaging-detectible moiety is modified from its biodistribution when administered without a biomodulator.

"Active agent" as used herein in the context of a therapeutic agent is a drug which is either bonded to a biomodulator or whose biodistribution is changed by being administered before, simultaneously with or after a biomodulator, such that the biomodulator and active agent are simultaneously bioeffective to treat aberrant tissue. The therapeutic-active agent may be linked to the biomodulator by either a cleavable or non-cleavable linkage.

The conjugation of the biomodulator to the "tactive" moiety can be accomplished using any of the plethora of conventional techniques. Generally, where a metal is involved this can be accomplished by attaching the metal to a binding molecule, typically a chelating agent. The resultant chelate is bound to the biomodulator. The order of these binding reactions is not critical. For instance, a chelate structure can be bound to a biomodulator by means of a substituent on the non-critical ring portion or other non-critical portion of a biomodulator as described below. Typical substituents include OH, COOH, $NH_2$, $CONH_2$, and many others. Linking the biomodulator and the chelating agent, carrier protein or drug can be by means of any of a host of conventional linkers. For thorough descriptions of useful chelating agents, linking moieties, chemical methods for effecting the couplings, etc., see, e.g., U.S. Pat. Nos. 4,352,751, 4,176,173, 4,310,507, 4,668,503, 4,986,979, 4,454,106; GB 2,109,407-A; G. E. Krejarek et al., Bioch. Biophy. Res. Comm. 77, 581 (1977); Sela et al. (U.S. Pat. Nos. 4,093,607 and 4,263,279); Schwartz (U.S. Pat. No. 4,647,671); Shen et al. (U.S. Pat. No. 4,631,190); Desphande et al. (Int. J. Rad. Appl. Instrum. [B] (England) 16, 587–597 (1988)); Quadri et al. (J. Nuc. Med. 27, p. 959 (Absr. #337)(1986)); Hoseman et al. (J. Nuc. Med. 12, 455–460 (1986)); Meares et al. (Intl. J. Cancer [Suppl.] U.S. 2, 99–102 (1988); A. R. Fritzberg et al., "Specific and Stable Labeling of Antibodies with Technetium-99m with a Diamide Dithiolate Chelating Agent," Proc. Natl. Acad. Sci. 85, 4025–4029 (1988); D. A. Scheinberg et al., "Tumor Imaging with Radioactive Metal Chelates Conjugated to Monoclonal Antibodies," Science 215, 1511–1513 (1982); A. R. Fritzberg, "Advances in $^{99m}$Tc-Labeling of Antibodies," Nucl. Med. 26, 7–12 (1987); D. J. Hnatowich et al., "DTPA-Coupled Proteins—Procedures and Precautions," Nucl. Med. Bio. 14, 563–568 (1987); D. J. Hnatowich et al., Science 220, 613 (1983); Manabe et al., Biochim. Biophys. Acta 883, 460 (1986).

Other methods of binding the active moiety to the biomodulator of course can also be used. Thus, radioactive iodine can be exchanged conventionally with non-radioactive iodine on the biomodulator, e.g., bonded to the ring portion of the molecule, especially an aryl ring. Other radioactive species, e.g., $^{99}$Tc, etc., can be bonded, e.g., via conventional "tagging" procedures well known in the art, e.g., according to Rhodes, U.S. Pat. No. 4,305,922; Crockford et al., U.S. Pat. No. 4,424,200; Alvarez et al., U.S. Pat. No. 4,741,900; EP-A-0 188 256; EP-A-0 289 187; EP-A-0 203 764; Fritzberg, Proc. Natl. Academy of Sciences U.S. 85, 4025–4029 (1988).

Thus, the biomodulators can be administered for the visualization of any portion of the body in which a given biomodulator is determined to concentrate, especially those suspected of being in an aberrant state in view of the general capability of biomodulators to concentrate therein, e.g., especially for the visualization of tumors, including cancerous and benign tumors such as soft tumors, such as leukemias and lymphomas, and solid tumors, such as melanomas, ovarian tumors, cervical tumors, breast tumors, lung tumors (small cell and non-small cell), colon and stomach tumors, hepatocellular tumors, pancreatic, midgut, bladder and prostate tumors, brain tumors, myelomas, and larynx tumors; senescent tissues and cells; injured tissue, especially containing endothelial cells for which biomodulators will enhance repair; defective immune cells; etc. Thus, this invention facilitates patient management by enabling the staging and evaluation of the extent of these aberrant states, such as metastasis of a tumor.

TNF-α was tagged using the ascorbic acid method developed by M. L. Thakur et al., "Tc-99m Labeled Monoclonal Antibodies: Evaluation of Reducing Agents," Internat. J. Nucl. Med. Biol. 18, 227–233, 1991; M. L. Thakur et al., "Tc-99m Labeled Monoclonal Antibodies for Immunoscintigraphy: Simplified Preparation and Evaluation," J. Immunol. Methods 137, 217–225 (1991).

By "abnormal tissue" herein is meant any tissue in a condition other than normal for a healthy host, e.g., mammals including humans, e.g., cancerous, diseased, injured, etc. Also included is senescent tissue whether due to the "normal" aging process or otherwise.

The biomodulators, per se or conjugates thereof, or in conjunction with unbound active agents as described above, can be administered in a manner analogous with other imaging agents in the conventional imaging and therapeutic methods, e.g., as described in Enhanced Magnetic Resonance Imaging, V. M. Runge, ed., C. V. Mosby Co. (1989) for MRI; e.g., in EP 188,256; Kozak et al., TIBTEC October 1986, 262; Radiotracers for Medical Applications, CRC Press, Boca Raton, Fla., for radiodiagnostics and/or for radiotherapy; in Positron Emission Tomography of the Brain, Springer Verlag 1983, for PET; and in J. W. Nowicky et al., "Macroscopic UV-Marking through Affinity," J. Tumor Marker Oncology 31, 463–465 (1988) demonstrate the property of biomodulators to concentrate or target malignant tissue for X-ray, in each case for imaging of various tissues described above. For example, they are typically administered prior to the performance of the imaging procedure. It is even possible for the administration to be simultaneous with the imaging where desired, e.g., in pharmacokinetic studies. The optimum time period required for localization at the target site and optimum image enhancement will also vary with biomodulator and/or conjugate and/or tissue and/or imaging modality and will also be routinely determinable. Of course, imaging will occur prior to significant clearance of the biomodulator from the site, which time period can also be routinely determined by those of skill in the art. Typically, biomodulators or conjugates will be administered 15 minutes to 4 hours prior to performing the imaging procedure since the biomodulators are, advantageously, localized rapidly at their target sites and then cleared rapidly therefrom, as discussed further below.

The agents of this invention may be administered alone, or more typically they may be administered in combination with one of the usual physiologically acceptable excipients, e.g., water, saline, buffers, surfactants, etc., by the usual routes, e.g., enterally, parenterally, e.g., i.v., i.m., subcutaneously. The optimum amount of the biomodulator may vary with the patient, the method of imaging employed, the location to be imaged, the timing of imaging, etc., and is routinely determinable by one of ordinary skill in the art. Typically, the amount of biomodulator or conjugate dosed for all the uses discussed herein above and below will be in the same range of the amounts thereof effective for observance of the therapeutic and other physiological effects of the biomodulators per se, e.g., their effects of normalizing cellular differentiative abnormalities, e.g., typically, 100 ng/kg–100 µg/kg. Since the imaging modalities are highly sensitive, these amounts will generally also be useful where imaging active moieties are coupled to the biomodulators. However, where desired, these active moiety dosages can be effectively increased by coupling more than one such moiety to a given biomodulator using the same conventional chemistry referred to above.

Analogous to the use of biomodulators for targeting imaging moieties, the same principles can be applied to the targeting of therapeutic moieties, i.e., drugs, by conjugation of the latter to biomodulators via the same basic conventional procedures mentioned above. In this case, it is often preferred that the drug be attached to the biomodulator via a preferably site-specific cleavable linker as are well known in the art. See, e.g., Sela et al., U.S. Pat. Nos. 4,093,607, 4,263,279; Schwartz, U.S. Pat. No. 4,647,671; Shin et al., U.S. Pat. No. 4,631,190; Desphande et al., Intd. J. Rad. Appl. Instrum. [B] (England), 16, 587–597 (1988); Quadri et al., J. Nuc. Med. 27, p. 959 (Abstract #337) (1986); Haseman et al., J. Nuc. Med. 12 455–460 (1986); Meares et al., Intl. J. Cancer [Suppl.] U.S. 2, 99–102 (1988); Hong et al., J. Med. Chem. 31, 1793 (1988).

Suitable such drugs include antitumor agents such as Ara-C, Melphalan, Methotrexate, and other folate analogs, Daunomycin, Doxorubicin, Mitomycins, Bleomycins, Mitoxantrone, Dactinomycin, etc., as well as toxins such as ricin, abrin, diptheria toxin, Pseudomonas exotoxin A, ribosomal inactivating proteins, mycotoxins, etc., but not limited thereto. Also applicable is a wide variety of other drug types, e.g., therapeutic agents in all of the major therapeutic areas including, but not limited to, anti-infectives, such as antibiotics and antiviral agents, analgesics and analgesic combinations, anthemidines, antiarthritics, antiasthmatic agents, anticonvulsants, antidepressants, antidiabetic agents, antidiarrheals, antihistamines, anti-inflammatory agents, antimigraine preparations, antimotion sickness, antinauseants, antineoplastics, antiparkinsonism drugs, antipruritics, antipsychotics, antipyretics, antispasmodics, including gastrointestinal and urinary; anticholinergics, sympathomimetics, xanthine derivatives, cardiovascular preparations including calcium channel blockers, beta-blockers, antiarrythmics, antihypertensives, diuretics, vasodilators including general, coronary, peripheral and cerebral, central nervous system stimulants, cough and cold preparations, decongestants, hormones, hypnotics, immunosuppressives, muscle relaxants, parasympatholytics, parasympathomimetics, psychostimulants, sedatives and tranquilizers.

In another aspect of this invention, a biomodulator can be administered to a host in order to alter the nature of the interaction with a drug (such as those discussed herein) of tissue in a host. This effect is believed to be derived from the same fundamental relationships between biomodulator and tissue as described above. Thus, a therapeutic agent subsequently contacting biomodulator-modified tissue will have a biodistribution different from that which it displays when interacting with tissue not treated with a biomodulator. In this aspect of the invention, the drug is not modified with an oligosaccharide.

Thus, when the therapeutically-active agent per se provides insufficient effect on or at tissue modifiable by a biomodulator in accordance with this invention as described herein, instead of administering such an agent alone, per this invention, there will also be administered a biomodulator of this invention. All details discussed above will correspondingly be applicable here. Thus, the latter may be administered before, simultaneously with or after the administration of the agent, as long as the resultant tissue modification of this invention is in existence at some time during the contact thereof with the therapeutic agent. Most typically, the biomodulator will be administered from about 15 minutes to about 4 hours prior to administration of the drug, longer and shorter times being satisfactory, as long as the effect of the biomodulator on the target tissue is still active when the active agent becomes bioavailable to such tissue, as is true for all aspects of this invention.

The particular combination of biomodulator/tissue to be selected in conjunction with the modification of the biodistribution of, and thus the therapeutic effect produced by, a particular modified drug will be routinely determinable in accordance with the principles and guidance described herein, e.g., with a few routine orientation experiments. For example, where it is desired to treat abnormal tissue, for reasons explained above, essentially any biomodulator will modify such tissue and concomitantly its interaction with a therapeutic agent. As a result, the corresponding treatment of such tissue and its environment will be different from that obtainable (if at all) in the absence of the biomodulator.

The invention will be most advantageous where a biomodulator/tissue/therapeutic agent combination is employed which results in a more concentrated treatment (rather than merely an alternative treatment regimen) for the abnormal tissue than is available with the drug without biomodulator added, as will generally be the case. Thus, another advantage of this invention is that it dramatically increases the usefulness of therapeutic agents per se which are commercially available, e.g., as discussed above, thus to circumvent specific problems associated with an agent in normal use (e.g., side effects) or to further accentuate an agent's desired characteristics.

This aspect of the invention will also be particularly applicable to abnormal tissue as discussed above, e.g., cancerous (or even benign) tumors, senescent cells, injured tissue, etc.

The amounts of biomodulator to be employed will be the same as described herein for the other aspects of the use of biomodulators; the amounts of the drugs to be used will be those conventionally employable.

Formulations of the biomodulator and drug are fully conventional using the usual pharmaceutically acceptable adjuvants, e.g., as described above. Similarly, other features of the administration of the biomodulator and/or drug are as described above or otherwise fully conventional.

For demonstration of the use of biomodulators as universal imaging agents see, e.g., Examples 1–3 herein.

In another aspect of this invention, a biomodulator can be administered to a host in order to alter the nature of the interaction with non-tissue-specific imaging-active agents of tissue in a host. This effect is believed to be derived from the same fundamental relationships between biomodulator and tissue as described above. Thus, a non-specific, imaging-active agent subsequently contacting biomodulator-modified tissue will have a biodistribution different from that which it displays when interacting with tissue not treated with a biomodulator.

Thus, as will be usually the case, when the non-specific, imaging-active agent per se provides no image or insufficient image contrast of tissue modifiable by a biomodulator in accordance with this invention as described herein, instead of administering such an imaging-active agent alone, per this invention, there will also be administered a biomodulator of this invention. The latter may be administered before, simultaneously with or after the administration of the non-specific, imaging-active agent, as long as the resultant tissue modification of this invention is in existence at some time during the contact thereof with the imaging-active agent. Most typically, the biomodulator will be administered from about 15 minutes to about 4 hours prior to administration of the non-specific, imaging-active agent.

The particular combination of biomodulator/tissue to be selected in conjunction with the modification of the biodistribution of, and thus the image contrast produced by, a particular imaging-active agent will be routinely determinable in accordance with the principles and guidance described herein, e.g., with a few routine orientation experiments. For example, where it is desired to image abnormal tissue, for reasons explained above, essentially any biomodulator will modify such tissue and concomitantly its interaction with a non-specific imaging agent. As a result, the corresponding image of such tissue and its environment will be different from that obtainable (if at all) in the absence of the biomodulator.

This first (or second) "view" of the tissue and the environment will provide valuable primary (or supplemental) information on the staging, extent and assessment of the abnormal tissue state. The invention will be most advantageous where a biomodulator/tissue/imaging agent combination is employed which results in an image of higher contrast for the abnormal tissue than is available with the imaging agent without biomodulator added, as will generally be the case with non-specific imaging agents. Thus, another advantage of this invention is that it dramatically increases the usefulness of non-specific imaging agents, preferably those which are commercially available, such as radiopharmaceuticals and magnetopharmaceuticals, e.g., by optimizing target-to-background ratios to enhance image quality.

This aspect of the invention is applicable to any imaging agent of any imaging modality which depends to any degree for its effect on interaction of the agent with tissue, e.g., which depends on the agent's biodistribution. These include, for example, agents useful for NMR, X-ray, radio- (e.g., gamma camera), ultrasonic, PET, etc., imaging. The principles of this aspect of the invention apply also to radiotherapy analogously to the other aspects of this invention discussed above, e.g., biodistribution of a radiotherapeutic agent can be advantageously modified per this aspect.

A multitude of such non-specific agents are well known or else readily determinable by skilled workers by reference to literature regarding substances, e.g., proteins, known and/or routinely predictable to be non-specific in vivo. Subramanion et al., Radiopharmaceuticals, Published by the Society of Nuclear Medicine, Inc. (1975); Tubis, et al., Radiopharmacy, John Wiley and Sons, New York (1976); and Rhodes et al., Basics of Radiopharmacy, C. V. Mosby, Saint Louis (1978). Herein, "non-tissue-specific" and variants thereof refer to agents which have essentially the same degree interaction with, especially of imaging enhancement effect on, essentially all body tissue with which they comes in contact. Especially useful agents for use in this invention include those suitable for radiodiagnostics, MRI, ultrasound or X-ray contrast, particularly, for example, without limitation, for nuclear medicine, radiolabeled proteins, e.g., radiolabeled human serum albumin, bovine serum albumin, etc.

Such agents may be endogenously detectable by a particular imaging modality, or may be exogenously labeled with an imaging-detectable label, e.g., $^{99m}$Tc-labeled protein.

The labeled non-specific agents can be made from available starting materials using standard chemical reactions which are routine to one of ordinary skill in the art. Thus, for example, $^{99m}$Tc-HSA is produced by labeling commercially available HSA with commercially available $^{99m}$Tc-labeling kits (e.g., Mediphysics, Paramus, N.J), according to package inserts. Other labeled non-specific imaging agents can be made analogously. For each agent, the exact nature of the bond between the imaging agent and the label is not critical, so long as the molecule as a whole is not denatured, not rendered insoluble, not rendered immunogenic, etc., and still functions as described.

The amounts of biomodulator to be employed will be the same as described herein for the other aspects of the use of biomodulators; the amounts of non-specific imaging agents will be essentially the same as those amounts usually employed with such agents or with analogous agents for the given imaging modality as conventionally performed, e.g., 0.1 mmol per kg for Gd-complexes or MRI; generally doses as are well known and described, for example, in the reference material cited above.

Formulations of the biomodulator and imaging agent are fully conventional using the usual pharmaceutically acceptable adjuvants, e.g., as described above. Similarly, other features of the administration of the biomodulator and/or imaging agent are as described above or otherwise fully conventional.

For demonstration of the effect of biomodulators in beneficially modifying the biodistribution of a non-specific imaging agent, see, e.g., Examples 4 and 5 herein.

The foregoing principles also fully apply to the coadministration of a biomodulator with a specific imaging agent, i.e., one which per se is selective for a given site in the body, such as Gd-DTPA for tumors, TNF, etc. This use is fully analogous to the coadministration of biomodulators with other specific active agents described above, i.e., drugs, and the principles and details described above in conjunction therewith are analogously applicable.

Also preferred are other tumor-specific active agents, which are specific for tumor tissue, e.g., tumor necrosis factor-α (TNF-α), which binds surface receptors on a variety of cell types. B. J. Culliton, "Gene Therapy: Into the Home Stretch," Science 249, 974–976 (1990).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, are hereby incorporated by reference.

EXAMPLES

Example 1

Radionuclide Imaging of Tumor Using $^{99m}$Tc-labelled Pokeweed Mitogen

Figure 2:
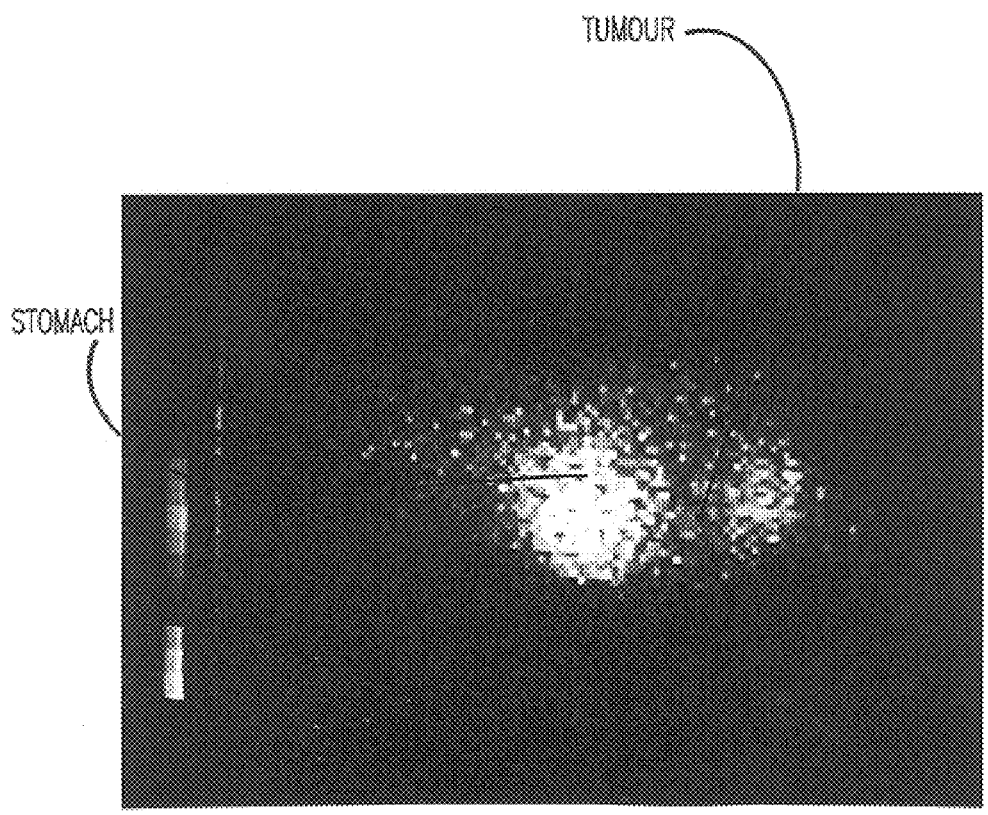
Figure 3:
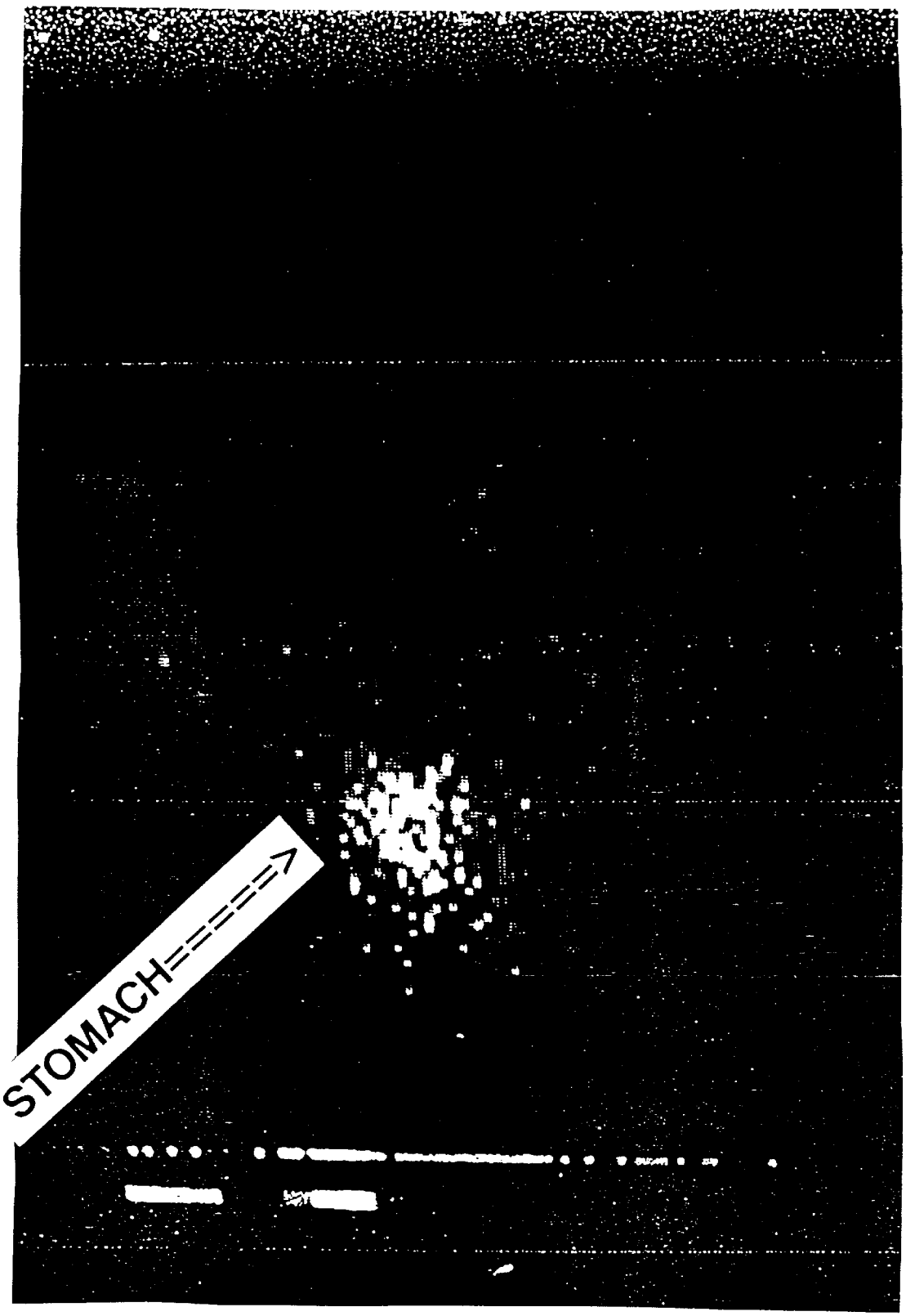
FIG. 3 is a radionuclide image of a mouse treated as in FIG. 1 except that the imaging was performed 24 hours after injection of $^{99m}$TC-labeled pokeweed mitogen (Tc-PWM).

Mice (C57/B1-6, 15–30 mg) were injected with 6×10$^5$ of allogenic B-16 melanoma cells 7 days (FIG. 1) or 10 days (FIG. 2) prior to injection of 2 to 5 mCi of $^{99m}$Tc-labeled pokeweed mitogen (Tc-PWM). Images were obtained by positron—a gamma camera over the back of the animal and an image was acquired for 1 min. at four hours post injection. Visualization of the tumor (indicated by arrow and documented by necropsy), stomach and intestines was observed. The Tc-PWM is rapidly cleared, as shown by FIG. 3, which reveals no tumor visualization in an image of a mouse treated as in FIG. 1, except that the imaging was performed 24 hours post-Tc-PWM injection.

The pokeweed mitogen used in the tests of all examples herein was obtained by the method of Waxdal.

Example 2
NMR Imaging of Tumor Using Pokeweed Mitogen

Figure 4:
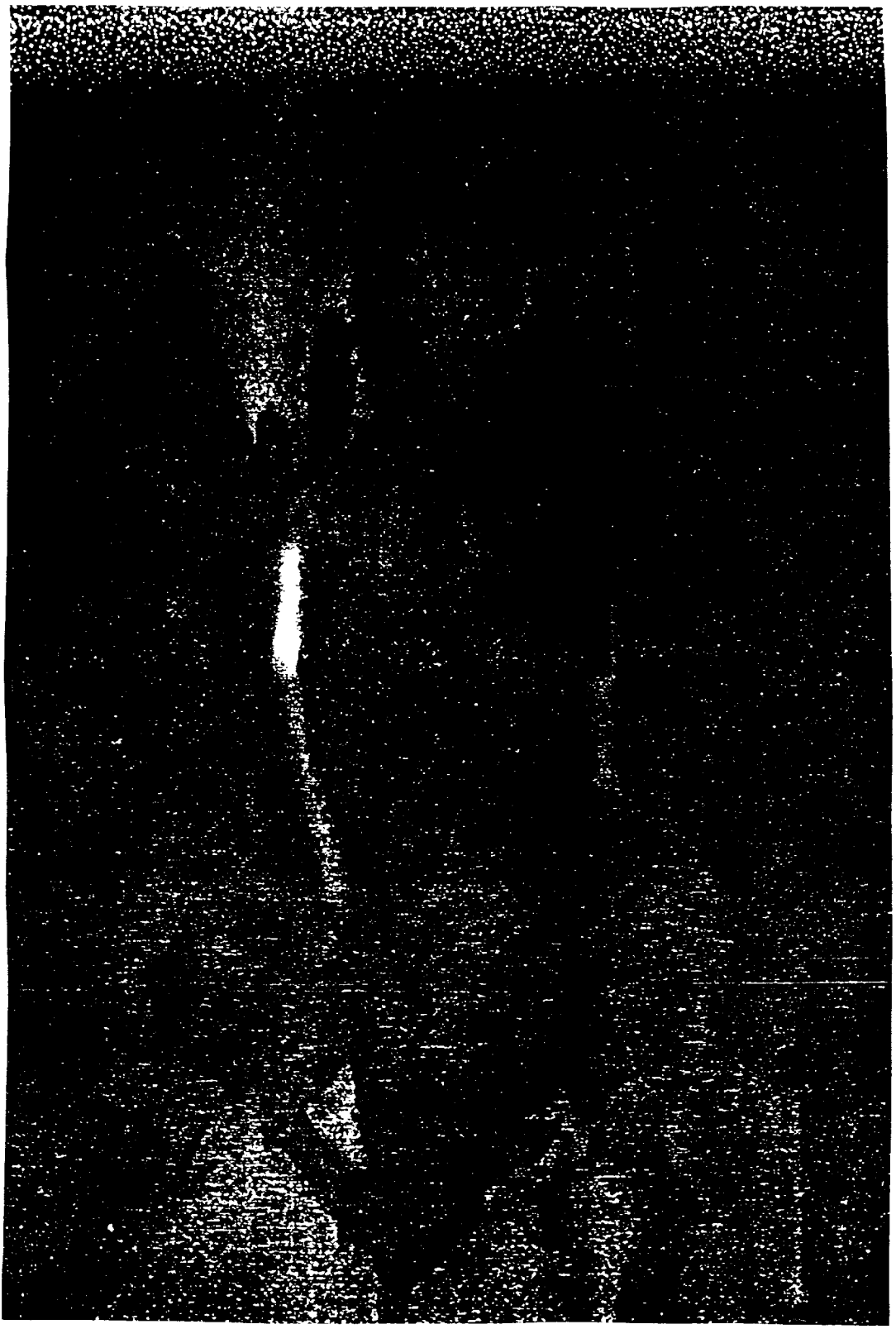
FIG. 4 is an NMR image of rats bearing canine glioma tumors taken 7 days post-implantation after administration of unlabeled pokeweed mitogen (PWM).
Figure 5:
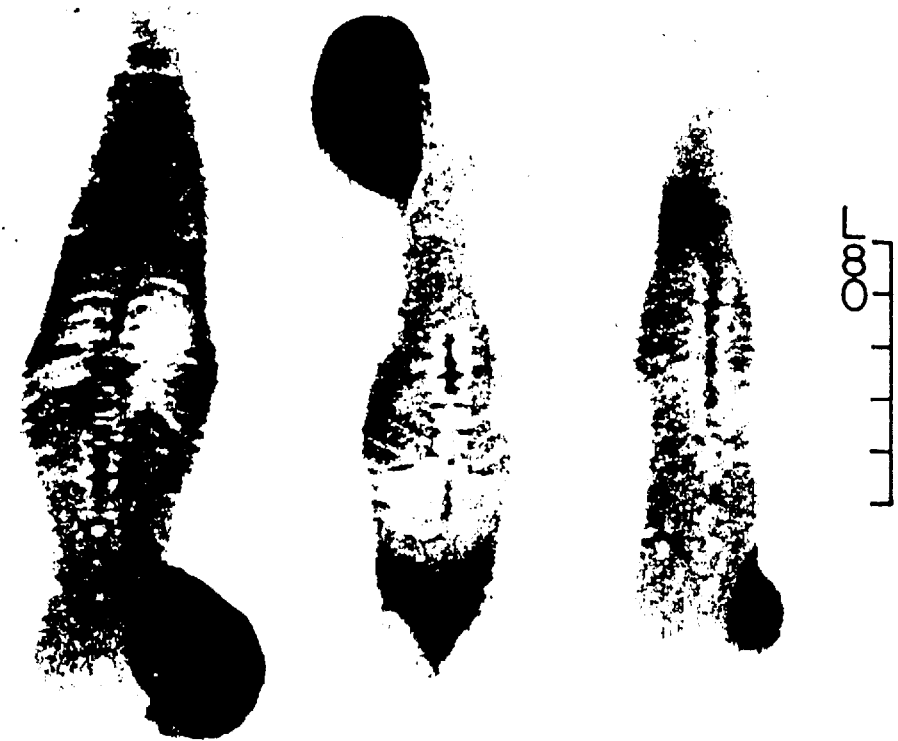
FIG. 5 is an NMR image showing the effect of unlabeled pokeweed mitogen on tumor $T_1$.

Three nude rats were implanted with canine glioma tumors in their left flank. FIG. 4 shows a photograph of the rats bearing the tumors on 7 days post-implantation, unlabeled PWM was administered. NMR imaging was performed as above at 4 hours post injection. Visualization of the tumors (FIG. 5) was observed as bright areas in the flank regions of the rats, showing that the biomodulator lowers $T_1$ of the treated tissue image, thereby enhancing image contrast.

Figure 6:
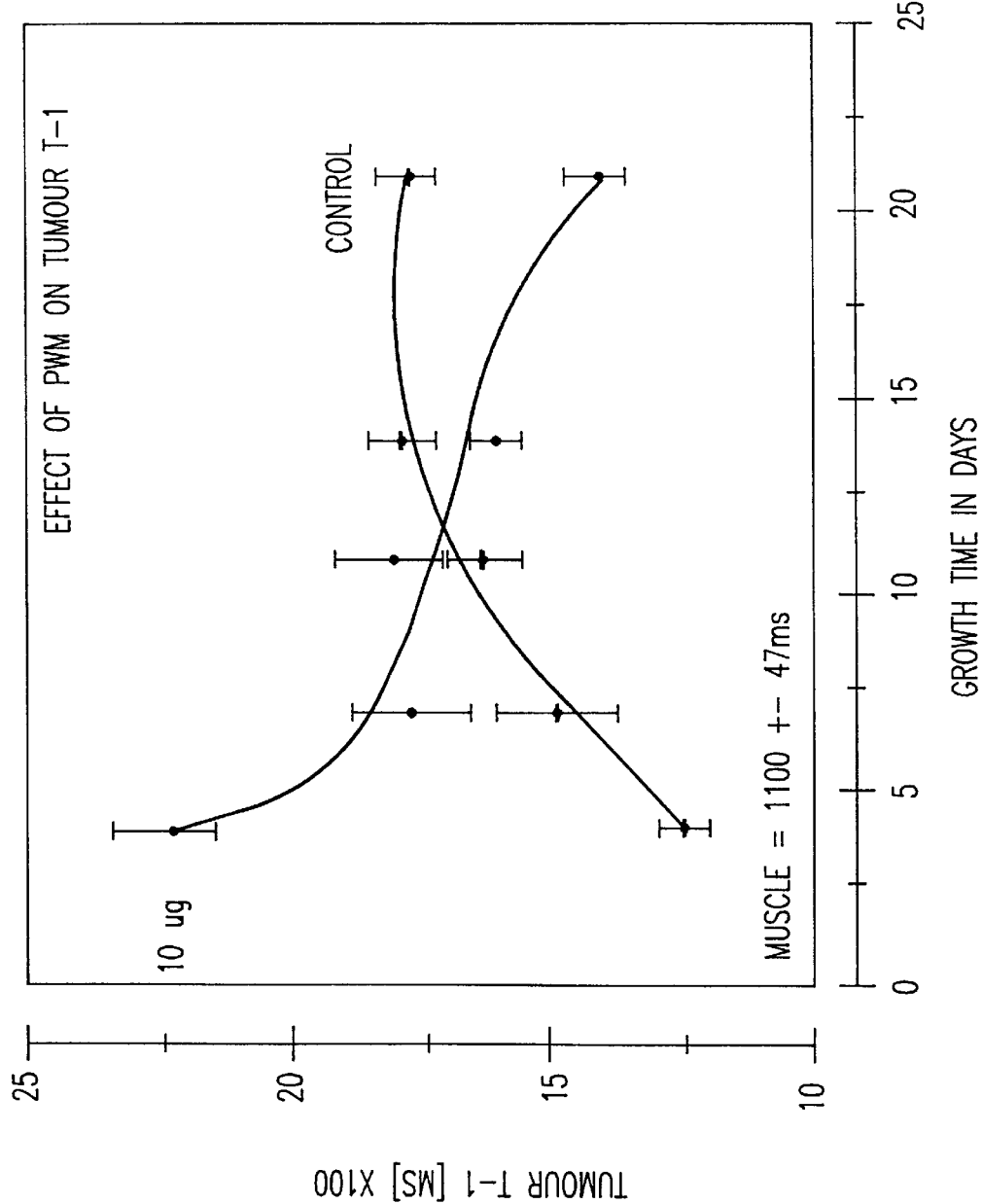
FIG. 6 is a plot showing the effect of treatment with unlabeled PWM on $T_1$ of the tumor over time.

Example 3
Biodistribution Studies of Pokeweed Mitogen a. The Effect on $T_1$ of Unlabeled PWM FIG. 6 shows that the $T_1$ measured on the tumor was enhanced tenfold by treatment with PWM, while the $T_1$ of normal muscle tissue remained at baseline levels, demonstrating that PWM is specific to the tumor, whereby the image of the latter is selectively enhanced.

b. $^{125}$I-labeled PWM

Figure 7:
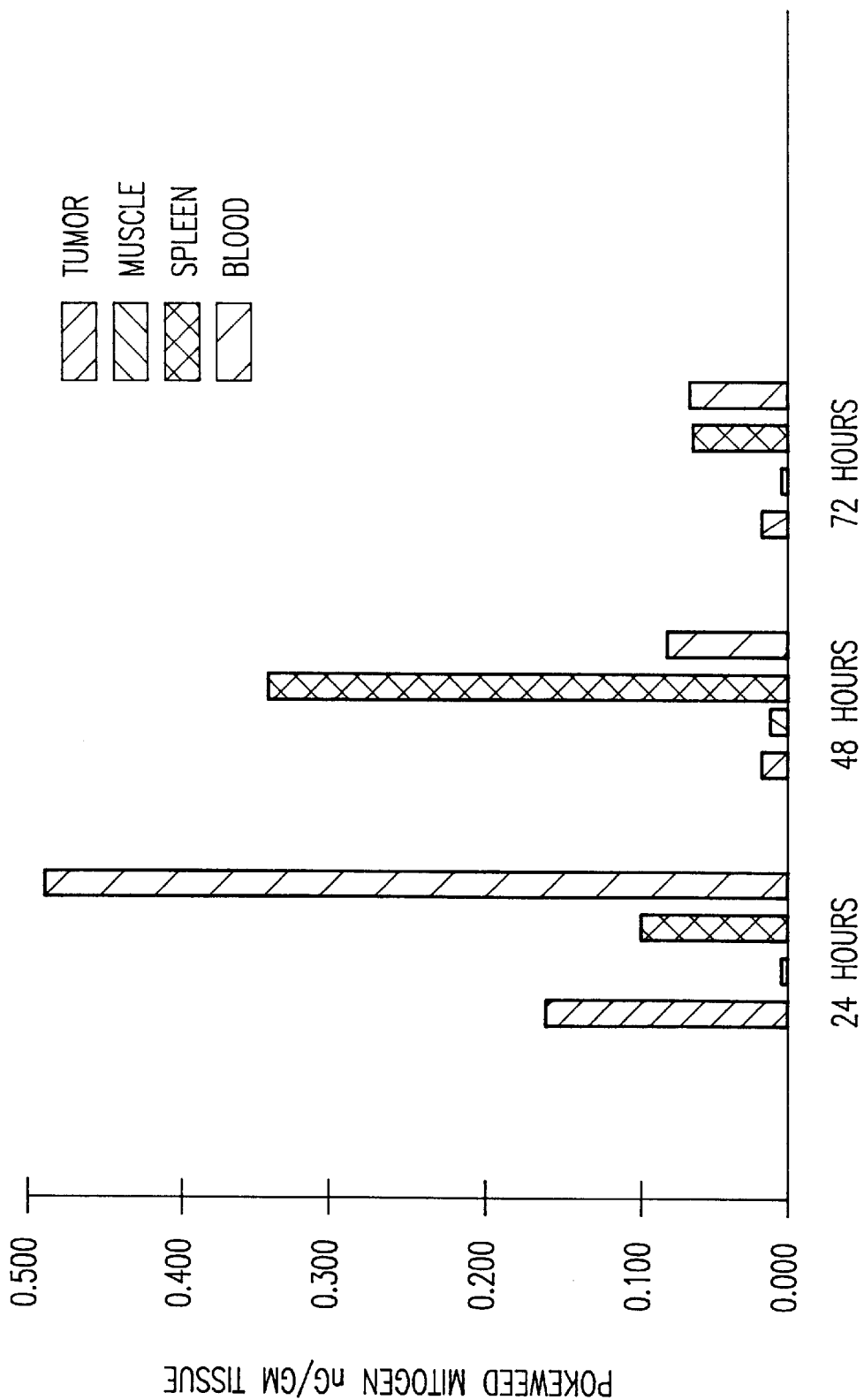
FIG. 7 shows the uptake of $^{125}$I-labeled PWM by canine glioma tumor cells in a nude rat.

FIG. 7 shows that $^{125}$I-labeled PWM is taken up very specifically by the canine glioma tumor cells in the nude rat, and is also washed out very quickly by 48 to 72 hours, whereby again the image of the cells is selectively enhanced.

c. Uptake of $^{99m}$Tc-PWM Versus $^{99m}$Tc-HSA

Figure 8:
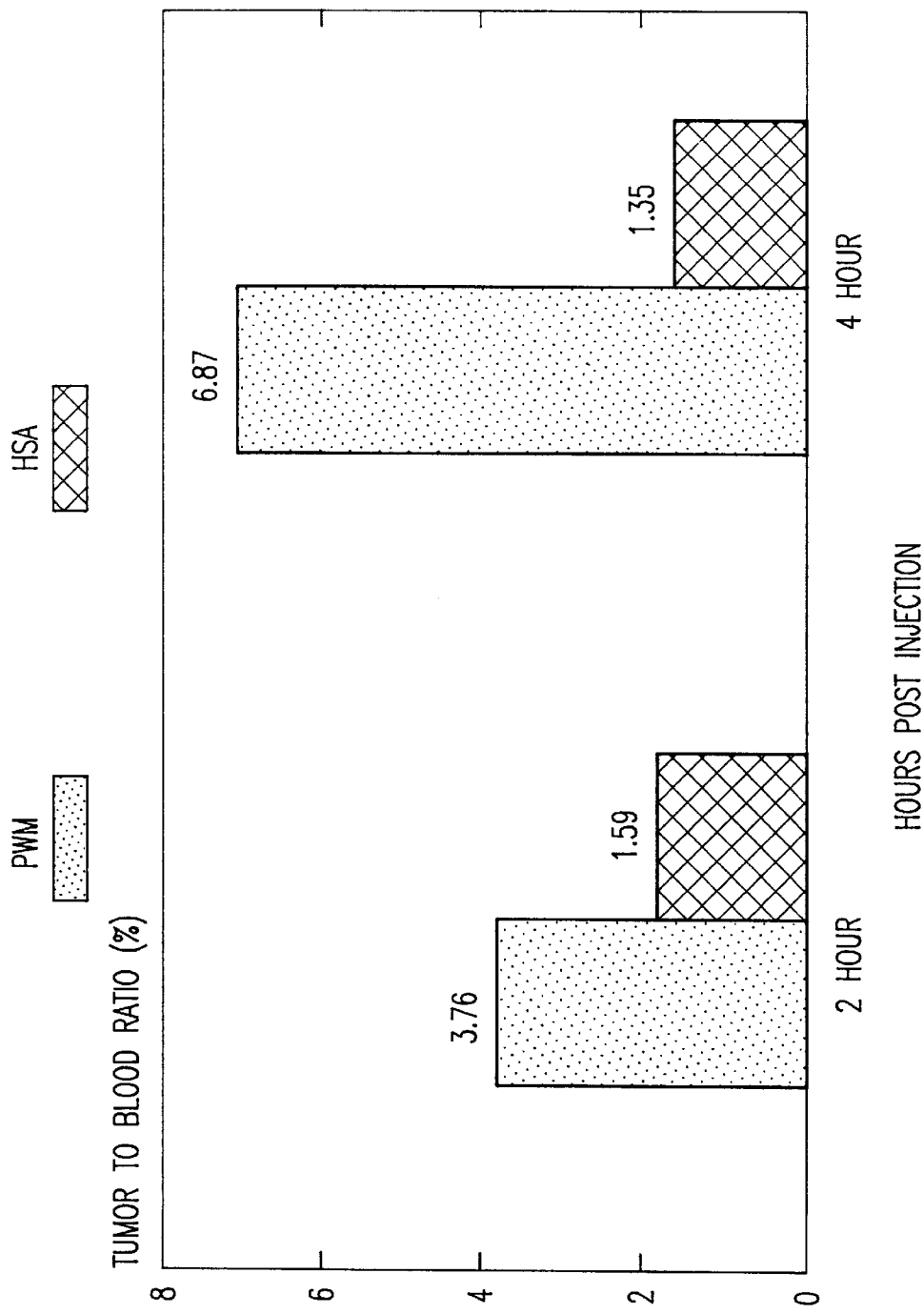
FIG. 8 is a bar graph of Tumor-to-Blood ratio of $^{99m}$Tc-PWM versus $^{99m}$TC-HSA.

Mice were injected with B-16 melanoma cells 7 days prior to intravenous injection of $^{99m}$Tc-PWM or $^{99m}$Tc-HSA (human serum albumin). Biodistribution studies were performed 2 and 4 hours later. At 2 hours post injection, the absolute percent uptake into the tumor was 0.41% for Tc-PWM, and 0.36% for Tc-HSA. At four hours post injection, the absolute uptake decreased to 0.25% of the injected dose for both agents. Visualization of the tumor, however, was not observed for the Tc-HSA-labeled material, but was observed for the Tc-PWM-labeled material. As can be seen from FIG. 8, the tumor to blood ratio for Tc-PWM was significantly higher than the tumor to blood ratio for Tc-HSA, providing a possible mechanism for the observed results.

Example 4
Tissue Localization of Otherwise Non-Specific Imaging Agent

A mouse (0.20 kg) was injected with B-16 melanoma cells in accordance with Example 1. 7 days later, 10 μg of pokeweed mitogen was injected into the mouse. Four hours later $^{99m}$Tc-human serum albumin (HSA) was injected. The resultant posterior gamma camera image is obtained of the tumor grown in the mouse. Comparison with the control image (following identical procedures except without pokeweed mitogen) showed significant image enhancement demonstrating localization of the non-specific agent, Tc-99m HSA into the tumor.

Figure 9:
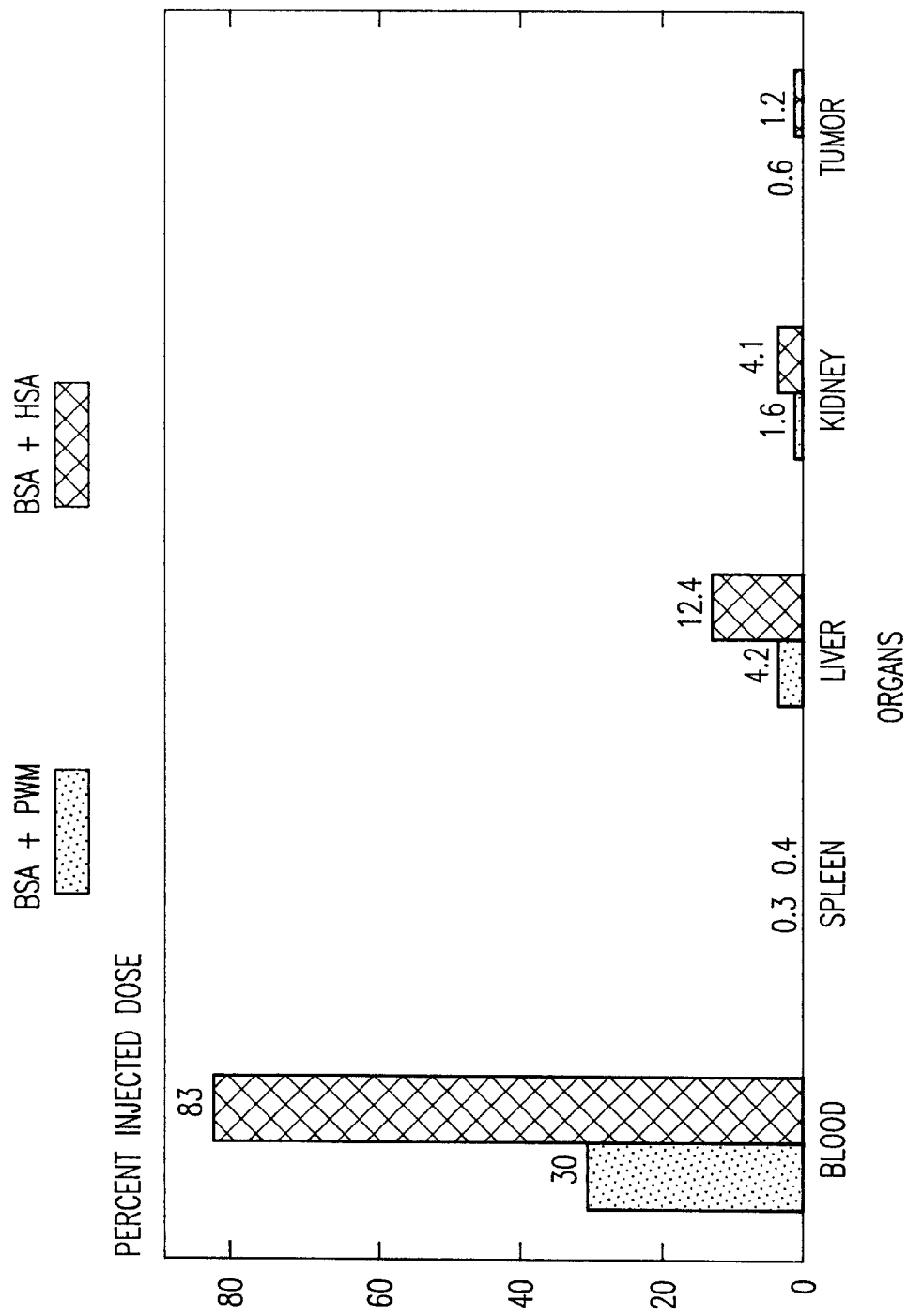
FIG. 9 is a bar graph showing the biodistribution after two hours of $^{125}$I-BSA co-injected with either $^{99m}$Tc-HSA or $^{99m}$Tc-PWM.
Figure 10:
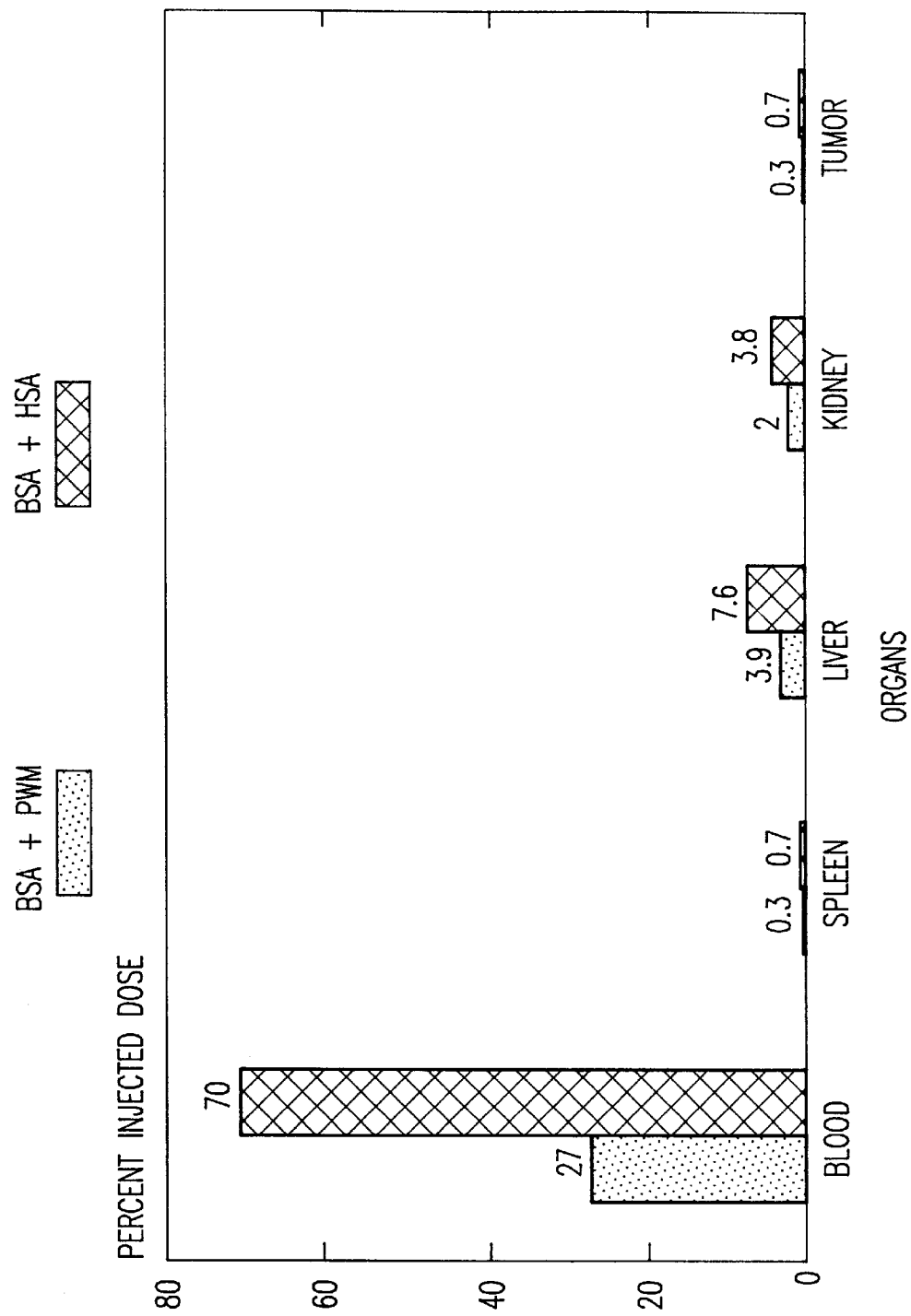
FIG. 10 is a bar graph showing the biodistribution after four hours of $^{125}$I-BSA co-injected with either $^{99m}$Tc-HSA or $^{99m}$Tc-PWM.

Example 5
Effect of a Biomodulator on the Biodistribution of an Non-specific Agent The results of biodistribution studies of mice injected with 6×10⁵ B-16 melanoma cells 7 days prior to the injection of Tc-99m labeled pokeweed (Tc-99m PWM) and I-125 bovine serum albumin (I-125 BSA) or Tc-99m labeled human serum albumin (Tc-99m HSA) and I-125 bovine serum albumin (I-125 BSA). Biodistribution studies at 2 hours (FIG. 9) and at 4 hours (FIG. 10) show significant differences in the distribution of the I-125 BSA depending upon what it was co-injected with.

Example 6
$^{125}$I-Pokeweed Mitogen Localization in Arthritic Tissue

Adjuvant induced polyarthritis in rats is an animal model that has been extensively used to study the pathogenesis of rheumatoid arthritis. These animal models have been used to identify drugs that have potential therapeutic efficacy. This model resembles the human disease both clinically and pathologically.

The model was created by injection of 0.1 mg of heat-killed *Mycobacterium butrycium* suspended in light mineral oil into the subplantar region of the right hindpaw. At the site of injection, an acute inflammation appears within 24 hours and reaches its maximum intensity approximately 4 days post induction and between days 10 to 12 a polyarthritis develops. $^{125}$I-PWM was labeled according to the iodobead method and injected into 4 rats 2 controls and 2 animals on day 15 post adjuvant arthritis induction.

The animals were anesthetized with pentobarbital, the femoral vein was isolated and the $^{125}$I-PWM was injected through the femoral vein and 2 hours later the animals were sacrificed and the left and right paws were removed and a blood sample was obtained. There was an injection problem in one of the control animals so the following results are a total of 1 control and 2 experimental animals.

|  | LEFT PAW | RIGHT PAW | L.Paw/ gm BLD | R.Paw/ gm BLD |
|---|---|---|---|---|
| Control | 30,297 cpm | 39,902 cpm | 2.57% | 3.39% |
| Arthritis | 35,307 cpm | 119,742 cpm | 3.16% | 10.73% |

| ARTHRITIC (n = 2)/CONTROL (n = 1) MODEL | | | |
|---|---|---|---|
| LEFT (cpm) | RIGHT (cpm) | Left (gms) | Right (gms) |
| 91.91% | 299.9% | 155% | 375.6% |

| Ratio RIGHT/LEFT PAW | |
|---|---|
| Control | 1.32 |
| Arthritis | 3.39 |

| | COUNTS PER MINUTE/GRAM TISSUE | |
|---|---|---|
| | LEFT PAW | RIGHT PAW |
| Control | 16,940 | 23,279 |
| Arthritis | 12,699 | 18,599 |

Conclusions

There is an increased activity in the arthritic paw over the control paw and between the more inflamed paw and the contralateral paw.

Example 7
Imaging Tumors with $^{99m}$Tc-labeled Tumor Necrosis Factor (TNF-α) and Biomodulators Balb/c mice bearing xenografts of human teratocarcinoma tumors induced by subcutaneous injections of live tumor cells 8 days previously were injected with 10 μg of Ukrain, pokeweed mitogen or 10K units of interferon. 15 hours later, they were injected i.v. with 10 μCi of $^{99m}$Tc-labeled TNF-α labeled using the ascorbic acid reduction method of M. L. Thakur. M. L. Thakur et al., "Tc-99m Labeled Monoclonal Antibodies: Evaluation of Reducing Agents," Internat. J. Nucl. Med. Biol. 18, 227–233 (1991). M. L. Thakur et al., "Tc-99m Labeled Monoclonal Antibodies for Immunoscintigraphy: Simplified Preparation and Evaluation," J. Immunol. Methods 137, 217–225 (1991). Mice were imaged at 1.5, 4 and 24 hours post injection of the $^{99m}$-labeled TNF-α and sacrificed for tissue distribution studies. The biomodulators, pokeweed mitogen and Ukrain, like the biologic response modifier, interferon, enhanced tumor to muscle ratios of radioisotope uptake at 1.5 hours compared to mice not receiving biomodulators or interferon, but not at 4 and 24 hours, indicating a time-dependent response to biomodulators.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of imaging tissue in a host, by a particular imaging modality, comprising administering to the host an amount of a biomodulator bonded to a moiety per se detectable by the modality effective for imaging of said tissue, wherein the biomodulator is:

(a) a compound of formula (I)

$$R^1-X-\underset{R^6}{\overset{R^4}{\underset{|}{C}}}-CH_2-\underset{R^7}{\overset{R^5}{\underset{|}{C}}}-CH_2-R^2 \quad (I)$$

wherein $R^1$ is an optically substituted aromatic, cycloaliphatic or heterocyclic ring system, $R^2$ is —CH$_2$OH, —CHO, —COOR$^3$, —COSR$^3$, —CONR$^8$R$^9$ or the corresponding lactone

[structure of lactone containing $R^4$, $R^5$, $R^7$, CH$_2$, O, C=O]

wherein $R^3$ is H or C$_{1-10}$-alkyl, $R^4$ and $R^5$ are each independently H or C$_{1-6}$-alkyl, $R^6$ and $R^7$ are each independently OR, NHR or SH wherein R is H or C$_{1-4}$-alkanoyl, $R^8$ and $R^9$ are each independently H or C$_{1-10}$-alkyl, and X is C$_{2-3}$-alkylene, C$_{2-3}$-alkenylene, C$_{2-3}$-alkynylene, a cyclopropylene group, —OCH$_2$— or —SCH$_2$—;

(b) a compound of formula (II) (swainsonine)

[structure (II) - indolizidine with HO, OH, OH, H, N]

or an indolizidine alkaloid having an electronically similar 1,3-diol structure;

(c) cellular activator and differentiator (CAD); or (d) pokeweed mitogen, and scanning the host with the image modality to obtain an image of the tissue.

2. A method of claim 1, wherein said tissue is abnormal tissue.

3. A method of claim 1 for radionuclide imaging of abnormal tissue of a host, comprising administering to the host a biomodulator bonded to a radioactive element, in an amount effective for radionuclide imaging of said tissue.

4. A method of claim 2 for magnetic resonance imaging of abnormal tissue of a host, comprising administering to the host a biomodulator bonded to a paramagnetic moiety, in an amount effective for magnetic resonance imaging of said tissue.

5. A method of claim 2 for X-ray or positron emission tomography imaging of abnormal tissue of a host, comprising administering to the host a biomodulator bonded respectively to an X-ray opaque or a positron emitting moiety, in an amount effective for X-ray or positron emitting tomography imaging of said tissue.

6. A method of claim 1, wherein the amount of said biomodulator is 100 ng/kg–100 μg/kg.

7. A method of claim 2 for visualizing a tumor.

8. A method of claim 1, wherein the biomodulator is pokeweed mitogen.

9. A method of claim 1, wherein said moiety is a specific agent.

10. A method of claim 1, wherein said moiety is a non-specific agent.

11. A method of claim 1, wherein the biomodulator is

[two chemical structures with OH, COO$^-$ groups] or having a 3S,5R; 3R,5R; or 3S,5S stereoconfiguration.

12. A method of enhancing the image of abnormal tissue in a host obtainable by a particular imaging modality, comprising administering to the host a non-tissue-specific imaging agent or a tissue-specific imaging agent for said modality and a biomodulator in amounts that are effective for enhancing the image of the abnormal tissue, wherein the biomodulator is:

(a) a compound of formula (I)

$$R^1-X-\underset{R^6}{\overset{R^4}{\underset{|}{C}}}-CH_2-\underset{R^7}{\overset{R^5}{\underset{|}{C}}}-CH_2-R^2 \quad (I)$$

wherein $R^1$ is an optionally substituted aromatic, cycloaliphatic or heterocyclic ring system, $R^2$ is —$CH_2OH$, —CHO, —$COOR^3$, —$COSR^3$, —$CONR^8R^9$ or the corresponding lactone

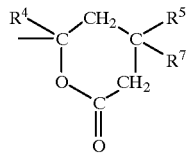

wherein $R^3$ is H or $C_{1-10}$-alkyl, $R^4$ and $R^5$ are each independently H or $C_{1-6}$-alkyl, $R^6$ and $R^7$ are each independently OR, NHR or SH wherein R is H or $C_{1-4}$-alkanoyl, $R^8$ and $R^9$ are each independently H or $C_{1-10}$-alkyl, and X is $C_{2-3}$-alkylene, $C_{2-3}$-alkenylene, $C_{2-3}$-alkynylene, a cyclopropylene group, —$OCH_2$— or —$SCH_2$—;

(b) a compound of formula (II) (swainsonine)

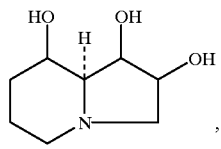

(II)

or an idolizidine alkaloid having an electronically similar 1,3-diol structure;

(c) cellular activator and differentiator (CAD); or (d) pokeweed mitogen, and scanning the host with the image modality to obtain an image of the tissue.

13. A method of claim 12, wherein the imaging agent is tissue-specific and is TNF-α.

14. A method of visualizing a tumor in a host using NMR imaging, comprising administering to the host an amount of a biomodulator effective to visualize the tumor, wherein the biomodulator is:

(a) a compound of formula (I)

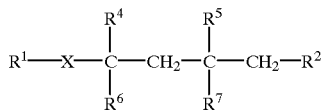

(I)

wherein $R^1$ is an optionally substituted aromatic, cycloaliphatic or heterocyclic ring system, $R^2$ is —$CH_2OH$, —CHO, —$COOR^3$, —$COSR^3$, —$CONR^8R^9$ or the corresponding lactone

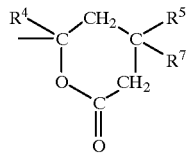

, wherein $R^3$ is H or $C_{1-10}$-alkyl, $R^4$ and $R^5$ are each independently H or $C_{1-6}$-alkyl, $R^6$ and $R^7$ are each independently OR, NHR or SH wherein R is H or $C_{1-4}$-alkanoyl, $R^8$ and $R^9$ are each independently H or $C_{1-10}$-alkyl, and X is $C_{2-3}$-alkylene, $C_{2-3}$-alkenylene, $C_{2-3}$-alkynylene, a cyclopropylene group, —$OCH_2$— or —$SCH_2$—;

(b) a compound of formula (II) (swainsonine)

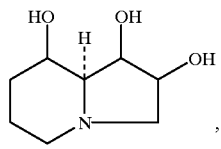

(II)

or an indolizidine alkaloid having an electronically similar 1,3-diol structure;

(c) cellular activator and differentiator (CAD); or (d) pokeweed mitogen, and scanning the host with NMR to visualize the tumor.

* * * * *